United States Patent
Lee et al.

(10) Patent No.: US 7,230,164 B2
(45) Date of Patent: Jun. 12, 2007

(54) GENE CONTROLLING FLOWERING TIME OF PLANTS AND METHOD FOR MANIPULATING FLOWERING TIME OF PLANT USING THE SAME

(75) Inventors: Jong Seob Lee, Seoul (KR); Yun Hee Kim, Anyang-si (KR); Eun kyung Choi, Seongnam-si (KR); So Yeon Yoo, Hanam-si (KR); Ji Hoon Ahn, Seoul (KR); Yang Do Choi, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 233 days.

(21) Appl. No.: 10/780,703

(22) Filed: Feb. 19, 2004

(65) Prior Publication Data

US 2005/0034194 A1 Feb. 10, 2005

(30) Foreign Application Priority Data

Feb. 20, 2003 (KR) ...................... 10-2003-0010772

(51) Int. Cl.
*C12N 15/82* (2006.01)
*A01H 5/00* (2006.01)
*A01H 5/10* (2006.01)

(52) U.S. Cl. ...................... 800/290; 800/278; 800/287; 800/298

(58) Field of Classification Search ............... 536/23.1, 536/23.6; 435/320.1, 410; 800/298, 278, 800/290
See application file for complete search history.

(56) References Cited

U.S. PATENT DOCUMENTS 6,177,614 B1 * 1/2001 Colasanti et al. ........... 800/290
6,225,530 B1 5/2001 Weigel et al.
6,444,877 B1 9/2002 Rottmann

OTHER PUBLICATIONS

Bowie et al, Science 247:1306-1310, 1990.*
McConnell et al, Nature 411 (6838):709-713, 2001.*
Kano-Murakami et al (1993, FEBS 334:365-368).*
Yamada et al (2002, NCBI Accession No. BT000874).*
Rounsley et al (2002, NCBI Accession No. AC005312).*
Poethig, R., "Phase Change and the Regulation of Shoot Morphogenesis in Plants." Science , vol. 250, 1990, pp. 923-930. Amer. Assn. for the Advancement of Science, Washington, D.C.
Simpson et al., "When to Switch to Flowering." Annu. Rev. Cell Dev. Biol., vol. 15, 1999 , pp. 519-550. Annual Reviews, Palo Alto, CA.
Araki, T., "Transition from vegetative to reproductive phase." Curr. Opin. Plant Biol., vol. 4, 2001, pp. 63-68. Current Biology, Ltd., London, England.
Levy, Y. et al., "The Transition to Flowering." The Plant Cell, vol. 10, 1998, pp. 1973-1989. American Society of Plant Physiologists, Rockville, MD.
Hepworth, S.R. et al., "Antagonistic regulation of flowering-time gene *SOC1* by CONSTANS and FLC via separate promoter motifs." EMBO Journal, vol. 21, 2002, pp. 4327-4337. Oxford University Press, Oxford, England.
Duval, M. et al., "Molecular characterization of *AtNAM*: a member of the *Arabidopsis* NAC domain superfamily." Plant Molecular Biology, vol. 50, 2002, pp. 237-248. Kluwer Academic, Dorcrecht, Holland.
Michaels, S. et al., "*Flowering Locus C* Encodes a Novel MADS Domain Protein That Acts as a Repressor of Flowering." The Plant Cell, vol. 11, May 1999, pp. 949-956. American Society of Plant Physiologists, Rockville, MD.

* cited by examiner

*Primary Examiner*—Stuart F. Baum
(74) *Attorney, Agent, or Firm*—Buchanan Ingersoll & Rooney, PC

(57) ABSTRACT

The present invention relates to a gene controlling the flowering time of plants, and a method for manipulating the flowering time of plants using the gene. More particularly, the present invention relates to a LOV1 gene controlling the flowering time of plants, which is isolated from *Arabidopsis thaliana*, and also to a method for either delaying the flowering time of plants by overexpressing the LOV1 gene in the plants, or inducing the early flowering of the plants by repressing the expression of the LOV1 gene in the plants.

5 Claims, 14 Drawing Sheets

FIG. 1A
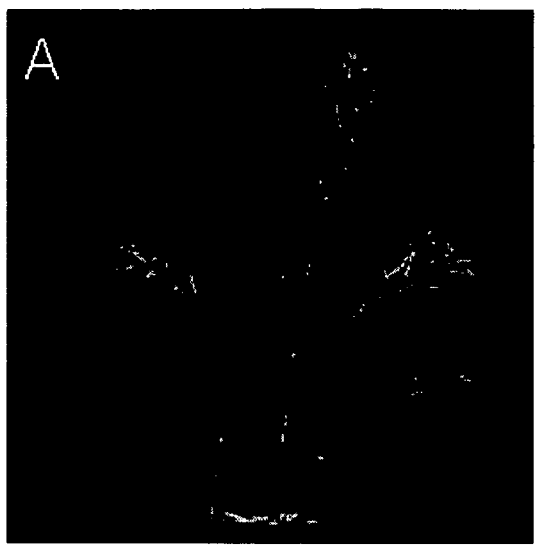 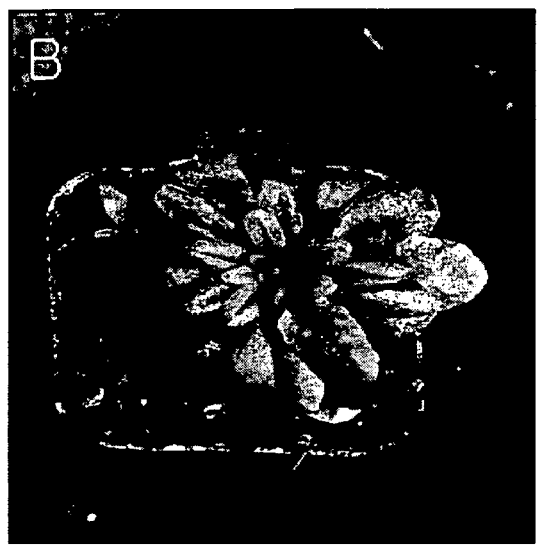

FIG. 1B
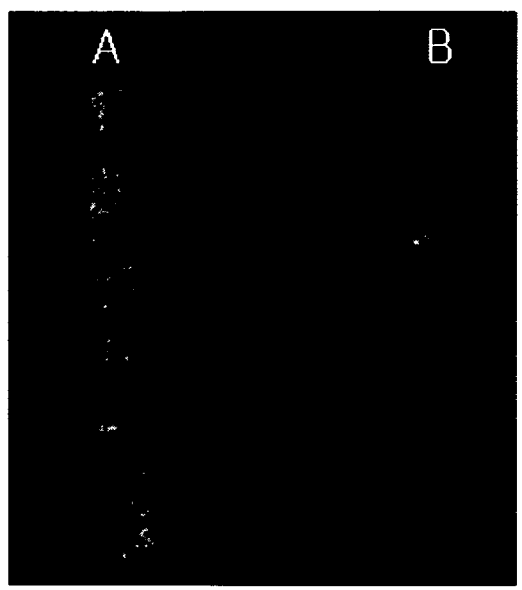 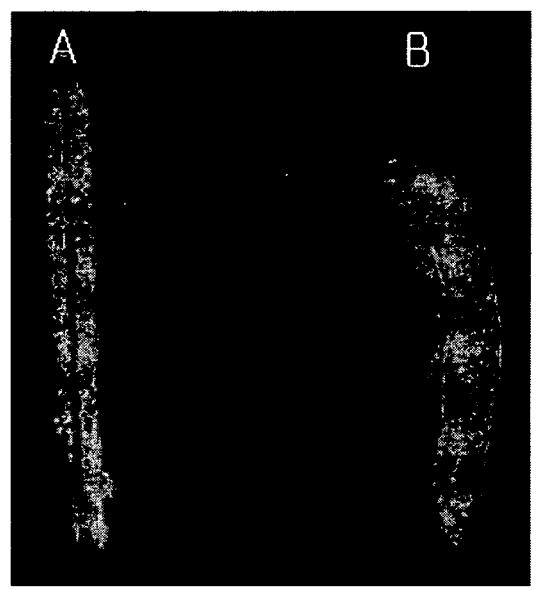

FIG. 3

```
                                                                                              *       *******
LOV1 (   1) maivssttsiipmsnqvnnekgiedndhrggQESHVQN-EDEADDHDHDMVMPGFRFHP
NAM  (   1) ----------------------------------ME----N-YQHFDCSDSN-LPPGFRFHP
CUC1 (   1) ------------------------------MDVDVFNgWGRPRFEDESLMPPGFRFHP
CUC2 (   1) ------------------------------MDIPYYH-YDHGG--DSQYLPPGFRFHP
                                            *  **  *********   *    ******  *****

LOV1 (  60) TEEELIEFYLRRKVEGKRFNVELITFLDLYRYDPWELPAMAAIGEKEWYFYVPRDRKYRN
NAM  (  23) TDEELITYYLLKKVLDSNFTGRAIAEVDLNKCEPWELPEKAKMGEKEWYFFSLRDRKYPT
CUC1 (  29) TDEELITYYLLKKVLDSNFSCAAISQVDLNKSEPWELPEKAKMGEKEWYFFTLRDRKYPT
CUC2 (  26) TDEELITHYLLRKVLDGCFSSRAIAEVDLNKCEPWQLPGRAKMGEKEWYFFSLRDRKYPT
            * **  ********  **       **    * ********  *    *******

LOV1 ( 120) GDRPNRVTTSGYWKATGADRMI-RSETSRPIGLKKTLVFYSGKAPKGTRTSWIMNEYRL-
NAM  (  83) GLRTNRATEAGYWKATGKDREIYSSKTSALVGMKKTLVFYRGRAPKGEKSNWVMHEYRLD
CUC1 (  89) GLRTNRATEAGYWKATGKDREIKSSKTKSLLGMKKTLVFYKGRAPKGEKSCWVMHEYRLD
CUC2 (  86) GLRTNRATEAGYWKATGKDREIFSSKTCALVGMKKTLVFYKGRAPKGEKSNWVMHEYRLE
                           **

LOV1 ( 178) ---PHHETEKYQK
NAM  ( 143) GKFAVHYISRSSK
CUC1 ( 149) GKFSYHYISSSAK
CUC2 ( 146) GKFSYHFISRSSK
```

FIG. 4
wild type *lov1-1D*
*LOV1*
25S rRNA

FIG. 7B

FIG. 8
(A) 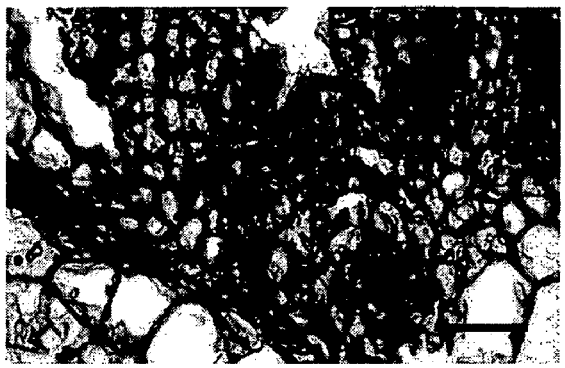
(B) 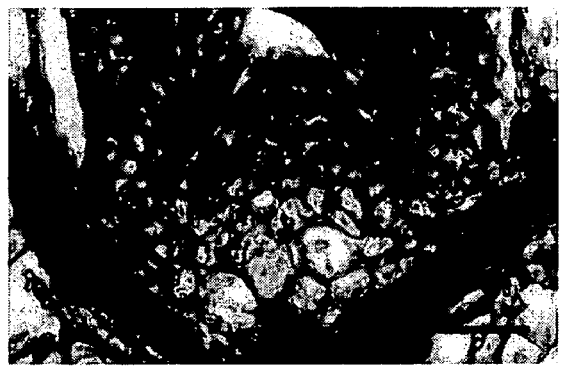

FIG. 10
wild type  *lov1-1D*
 *LOV1*
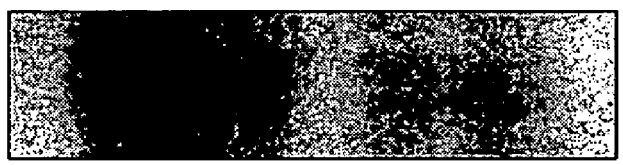 *AGL20*
 *FLC*
 25S rRNA

GENE CONTROLLING FLOWERING TIME OF PLANTS AND METHOD FOR MANIPULATING FLOWERING TIME OF PLANT USING THE SAME

The application claims the priority of Korean Patent Application No. 10-2003-0010772 filed on Feb. 20, 2003.

FIELD OF THE INVENTION

The present invention relates to a gene controlling the flowering time of plants, and a method for manipulating the flowering time of plants using the same. More particularly, the present invention relates to a LOV1 gene controlling the flowering time of plants, which is isolated from *Arabidopsis thaliana*, and also to a method of either delaying the flowering time of plants by overexpressing the LOV1 gene in the plants, or inducing the early flowering of the plants by suppressing the expression of the gene LOV1 in the plants.

BACKGROUND OF THE INVENTION

The flowering of plants causes a phase transition, which converts the growth of plants from vegetative growth to reproductive growth Most of plants have a mechanism by which the plant's flowering can be controlled such that the flowering occurs at a suitable time. This control mechanism of flowering time is influenced by genetic factors within plants, and external environmental factors (Lang A., *Encyclopedia of Plant Physiology*, Springer-Verlag, 1371–1536, 1965; Napp-Zinn K., *In Manipulation of Flowering*, London, Buttrworth, 123–132, 1987; and Poethig R. S., *Science*, 250: 923–930, 1990).

Recently, various studies on a control mechanism of plant's flowering time are being actively conducted on the dicot plant *Arabidopsis thaliana* through various genetic and molecular biological approaches. As a result, about 80 genetic loci involved in controlling the flowering time in *Arabidopsis thaliana* have been found, and four pathways controlling the flowering time have been found (Simpson et al., *Annu. Rev. Cell Dev. Biol.* 15:519–550, 1999; and Araki T., *Curr. Opin. Plant Biol.* 4:6368, 2001). The first pathway is a photoperiod-dependent pathway or a long day pathway, and genes known to be involved in this pathway include genes encoding a photoreceptor, such as phytochrome or cryptochrome, GI (GIGENTEA), CO (CONSTANS), FT (Flowering locus T), FWA (Flowering Wageningen), SOC1 (Suppressor of CO overexpression 1; AGL20) (Yaron Y. et al., *The Plant Cell*, 10:1973–1989, 1998). The second pathway is a vernalization pathway where the plant's flowering is promoted when plants are exposed to low temperature for a long time. As genes known to be involved in this pathway, genes, such as VRN1 (Reduced Vernalization Response 1), VRN2 (Reduced Vernalization Response 2), FRI (Frigida), and FLC (Flowering locus C), were cloned. The third pathway is an autonomous pathway where the plant's flowering is controlled while influencing both long-day conditions and short-day conditions. Genes involved in this pathway include FCA (Flowering locus CA), FVE, LD (Lurninidepedens) (Yaron Y. et al., *The Plant Cell*, 10:1973–1989, 1998). The fourth pathway is a gibberellic pathway where GA (gibberellic acid), a kind of plant hormones, plays an essential role and the pathway mainly having an effect on short-day conditions. It is reported that genes, such as GA1, GAI (GA Insensitive) and RGA (Repressor of gal-3) are involved in this pathway, and mainly, genes involved in the biosynthesis of GA hormones, or genes involved in the signal transfer of GA hormones, participate in this pathway (Araki T., *Curr. Opin. Plant Biol.*, 4: 6368, 2001).

Attempts to artificially control the flowering time of plants using the genes involved in controlling the flowering time in plants, which were found as described above, are being conducted. Artificially controlling the flowering time of plants has a very important meaning in scientific viewpoints or industrial terms, such as agricultural or horticultural fields. The scientific study of a flowering control mechanism is very useful in establishing the initial embryogenesis and also organ development in higher plants. Furthermore, promoting the flowering time of horticultural plants in industrial terms allows flowers and seeds to be produced within a short time. Also, the flowering time of crops can be delayed to continuously induce the vegetative growth of the crops so that the production of useful portions from the crops can be increased.

U.S. Pat. No. 6,225,530 discloses an FT (flowering locus T) gene controlling the flowering time of plants, which is isolated from *Arabidopsis thaliana*, and also discloses a polypeptide encoded by the FT gene, and a method for controlling the flowering time of plants using the FT gene. Furthermore, U.S. Pat. No. 6,444,877 discloses a LSAG gene controlling the flowering time of plants, which is isolated from *Liquidambar styraciflua* (Sweetgum), and also a method for controlling the flowering time using the LSAG gene. Korean patent No. 319395 discloses a GIGANTEA gene controlling the biological clock and flowering time of *Arabidopsis thaliana*.

However, since it is believed that the control of a plant's flowering time occurs through a significantly complex process and various genes which were not completely found are involved in this process, studies on new genes involved in the control of a plant's flowering time, and functions thereof, are required.

SUMMARY OF THE INVENTION

During our studies on new genes involved in a control mechanism of flowering time, a LOV1 gene with a function of delaying the flowering of *Arabidopsis thaliana* upon overexpression was isolated from *Arabidopsis thaliana* by activation tagging screen, and it was found that the LOV1 gene can be used to control the flowering time of plants. On the basis of this discovery, the present invention was completed.

Therefore, an object of the present invention is to provide an isolated polynucleotide encoding a polypeptide controlling the flowering time of plants.

Another object of the present invention is to provide a recombinant vector comprising the polypeptide.

Still another object of the present invention is to provide a cell comprising the polypeptide.

Still another object of the present invention is to provide a plant comprising the polypeptide.

Still another object of the present invention is to provide plant tissue or seed derived from the plants.

Still another object of the present invention is to provide a method of delaying the flowering time of plants, comprising the step of introducing the polypeptide into the plants to overexpress it in the plants.

Still another object of the present invention is to provide a method of promoting the flowering time of plants, comprising the step of introducing an antisense molecule into the plants to inhibit the expression of the polypeptide in the plants.

Still another object of the present invention is to provide a method for identifying a compound controlling the flowering time of plants, comprising the steps of culturing a recombinant cell expressing the polypeptide and a candidate substance; and measuring the effect of the candidate substance on the expression of the polypeptide.

Still another object of the present invention is to provide a method for screening a gene controlling the flowering time of plants using the polypeptide.

BRIEF DESCRIPTION OF THE DRAWINGS

FIG. 1A is a photograph showing wild type *Arabidopsis thaliana* and lov1-1D mutants, which were cultivated for two months under long-day conditions (A: wild type *Arabidopsis thaliana*, B: lov1-1D mutants).

FIG. 1B is a photograph showing the difference in silique shape between wild type *Arabidopsis thaliana* and lov1-1D mutants (A: wild type *Arabidopsis thaliana*, B: lov1-1D mutants).

FIG. 3 shows the comparison between the NAC domain conserved in a LOV1 gene (SEQ ID NO 2, from position 1 to 185) for controlling the flowering time of the present invention and the NAC domains of NAM, CUC1 and CUC2 genes (SEQ ID NOS: 10–12) (*: conserved base sequence).

FIG. 4 is the result of Northern blot analysis showing the expression level of a LOV1 gene in wild type *Arabidopsis thaliana* and lov1-1D mutants (25S rRNA: internal control).

FIG. 7B shows the results of GUS activity analysis in the inflorescence meristem, axillary meristem and embryogenesis of a transgenic plant introduced with a LOV1 promoter-GUS gene fusion construct (A: inflorescence meristem, B: axillary meristem, C: embryogenesis, scale bar: 50 μm).

FIG. 8 is a stereomicroscopic photograph for the cross-sections of shoot apical meristem of wild type *Arabidopsis thaliana* and lov1-1D mutants (A: wild type *Arabidopsis thaliana*, B: lov1-1D mutants, scale bar: 20 μm).

FIG. 10 is the result of Northern blot analysis showing the expression levels of LOV1, AGL20 and FLC genes in wild type *Arabidopsis thaliana* and lov1-1D mutants (25S rRNA: internal control).

DETAILED DESCRIPTION OF THE INVENTION

Figure 2:
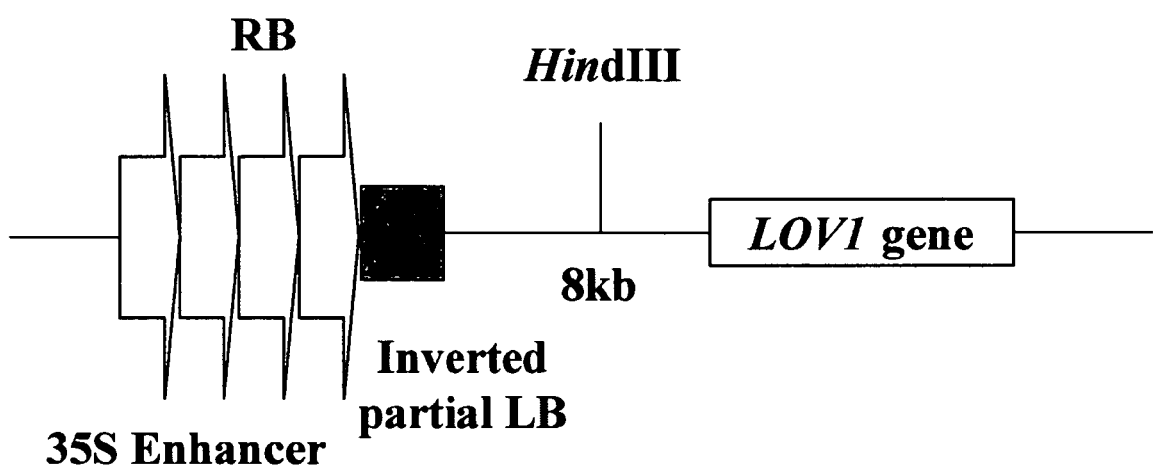
FIG. 2 is a schematic diagram showing the location of T-DNA inserted into the genome of the lov1-1D mutants (RB: the right border of T-DNA; and LB: the left border of T-DNA).

To achieve the above objects, the present invention provides an isolated polynucleotide encoding a polypeptide controlling the flowering time of plants, wherein the polypeptide comprising an amino acid sequence with at least 70% sequence homology to an amino acid sequence of SEQ ID NO: 2, or comprising the amino acid sequence of SEQ ID NO: 2.

Also, the present invention provides a recombinant vector comprising the polynucleotide.

Also, the present invention provides plants comprising the polynucleotide.

Also, the present invention provides a method for manipulating the flowering time of plants using a gene controlling the flowering time of plants. The method is characterized by overexpressing the polypeptide in plants to delay the flowering time of the plants, or inhibiting the expression of the polypeptide in plants to promote the flowering time of the plants.

Also, the present invention provides a method for identifying a compound controlling the flowering time of plants, the method comprising the steps of: culturing a recombinant cell expressing the polypeptide and a candidate substance; and measuring the effect of the candidate substance on the expression of the polypeptide. The compound may be one promoting or inhibiting the expression of the polypeptide.

Furthermore, the present invention provides a method for screening a gene controlling the flowering time of plants using a gene and promoter controlling the flowering time of the plants.

Hereinafter, the present invention will be described in detail.

To investigate a gene involved in controlling the flowering time of plants the present inventors screened mutants with a delayed flowering character in *Arabidopsis thaliana*, using an activation-tagging screen. The activation-tagging screen used in the present invention is a known method for obtaining gain-of-function mutants using enhances from 35S promoter of the cauliflower mosaic virus. The enhancers can activate the transcription of surrounding genes even in a state where the 35S promoter enhancer sequence is relatively far away (Weigel et al., *Plant Physiology*, 122: 1003–1013, 2000). More concretely speaking, the activation-tagging screen is a method in which an activation tagging vector with a screening marker, a replication origin, and an antibiotic- or herbicide-resistant gene in T-DNA and with four 35S CaMV enhancers within the right border of the T-DNA is randomly introduced into the *Arabidopsis thaliana* genome, the transcription of surrounding genes is activated, plants with a gain-of-function phenotype are screened, and then, the genomic DNA of the plants is collected to clone the transcription-activated genes.

In an embodiment of the present invention, in order to screen mutants with delayed flowering in *Arabidopsis thaliana*, mutants were produced using a pSKI015, an activation tagging vector, that is commonly used in the art. Then, among grown individuals, mutants with delayed flowering were selected with the naked eye, and the selected mutants were termed "lov1-1D mutants". Next, to confirm the delayed flowering character of the lov1-1D mutants, the flowering time of the lov1-1D mutants was compared to the flowering time of wild type *Arabidopsis thaliana*. As a result, in the mutants, formation of a flower axis was two months later than the wild type *Arabidopsis thaliana*, and there was also a case where the flower stalk was not formed even after two months. Moreover, in the lov1-1D mutants, it could be seen that an abnormal silique shape appeared and the number of rosette leaves was increased as compared to the wild type *Arabidopsis thaliana*. It was believed that this change in phenotype occurred because the vegetative growth period in the mutants was lengthened as compared to the wild type *Arabidopsis thaliana*.

In another embodiment of the present invention, a gene involved in controlling the flowering time of plants was isolated from the lov1-1D mutants by plasmid recovery, and its base sequence was analyzed. It was found that the isolated gene had a total genome size of 2,606 bp and an ORF (open reading frame) encoding 379 amino acids. The present inventors examined the sequence homology between the gene of the present invention and other known genes on the Genbank Database. As a result, the gene of the present invention showed the homology with the NAM, CUC1 and CUC2 genes of Perunia hebrida that are the members of the NAC domain gene family. Namely, it could be found that the first and second exons were conserved in the inventive gene and the NAC domain gene family. Thus, it was believed that the gene according to the present invention is present only in plants and belongs to the NAC domain gene family, which plays an important role in plant development processes, such as the maintenance of an apical meristem or the separation of a cotyledon. Thus, the present inventors termed the gene of the present invention "LOV1" (Long Vegetative phase 1). Furthermore, the present inventors inferred an amino acid sequence from the determined gene base sequence using Mac DNASIS program. The amino acid sequence is represented by SEQ ID NO: 2.

In another embodiment of the present invention, in order to identify whether the delayed flowering phenotype occurring in the lov1-1D mutants is due to the activation of the LOV1 gene, Northern blot analysis was performed using the LOV1 gene as a probe. The result showed that the LOV1 gene was overexpressed in the lov1-1D mutants as compared to the wild-type *Arabidopsis thaliana*.

Also, in order to examine temporal and spatial expression patterns of the LOV1, the present inventors extracted DNA from various tissues of wild type *Arabidopsis thaliana* and conducted a Northern blot analysis for the extracted DNA using a LOV1 gene-specific probe. The results of the Northern blot analysis showed that the LOV1 gene was expressed mainly in a stem and basically expressed in all the tissues. Furthermore, the present inventors constructed a nucleic acid construct with a LOV1 gene promoter-GUS (beta-glucuronidase) gene fusion system, a transformed *Arabidopsis thaliana* with an expression vector containing this construct, and then analyzed GUS gene activity, thereby examining the expression pattern of the LOV1 gene. As a result, it could be found that the LOV1 gene was strongly expressed in the shoot apical meristem of vegetative growth stage plants. In addition it could be found that the expression of the LOV1 gene continuously occurred after flowering and during embryogenesis.

Moreover, in another embodiment of the present invention, the difference in anatomical structure between the shoot apical meristems of wild type *Arabidopsis thaliana* and lov1-1D mutants was examined. The results showed that the cross-sections of the shoot apical meristems and leaves of the lov1-1D mutants had increased cell size and number as compared to the wild type *Arabidopsis thaliana*. Thus, it could be found that, in the lov1-1D mutants, vegetative growth period was lengthened while flowering was delayed.

Furthermore, in order to examine the genetic correlation between the love gene of the present invention and other known genes controlling the flowering time, the expression levels of flowering-promoting gene AGL20 and flowering-inhibiting gene FLC in the lov1-1D mutants were examined by Northern blot analysis. The results showed that the expression level of the AGL20 gene in the lov1-1D mutants was reduced as compared to that in the wild type *Arabidopsis thaliana*, and there was no change in the expression of the FLC gene. This suggests that the overexpression of the LOV1 gene reduced the expression of the AGL20 gene to delay flowering.

Accordingly, the present invention provides a novel polynucleotide encoding a polypeptide controlling the flowering time of plants. The polypeptide of the present invention includes a polypeptide isolated from *Arabidopsis thaliana* and having an amino acid sequence of SEQ ID NO: 2, and also functional equivalents thereof. As used herein, the term "functional equivalents" refer to polypeptide having at least 70%, preferably at least 80%, and more preferably at least 90% sequence homology to the amino acid sequence of SEQ ID NO: 2 as a result of the addition, substitution or deletion of an amino acid and the proteins with the substantially identical physiological activity to the protein of SEQ ID NO: 2, in which the proteins have. As used herein, the term "substantially identical physiological activity" means the activity of delaying the flowering of plants upon overexpression in the plants, and more preferably, the activity of inhibiting the expression of flowering-promoting gene A AGL20 to delay the plant's flowering. Preferably, the polypeptide controlling the flowering time of plants has an amino acid sequence of SEQ ID NO: 2.

Furthermore, the polynucleotide controlling the flowering time of plants of the invention includes both genomic DNA and cDNA encoding the polypeptide. Preferably, the polynucleotide of the present invention may include a sequence of SEQ ID NO: 1. More preferably, the polynucleotide controlling the flowering time of plants of the present invention is a LOV1 gene represented by SEQ ID NO: 3. Furthermore, the polynucleotide according to the present invention is characterized in that it has a conserved NAC domain and represses the flowering-promoting gene AGL20.

The polynucleotide controlling the plant's flowering time according to the present invention can be inserted into a suitable expression vector to transform plant cells. As used herein, the term "expression vector" means plasmids, virus or other vehicle known in the art that has been manipulated by insertion or introduction of the polynucleotide sequence of the present invention. The polynucleotide sequence of the present invention can be operably linked to an expression control sequence, and the sequence operably linked to the expression control sequence can be included within a single expression vector containing both a selection marker and a replication origin. As used herein, the term "operably linked" may mean that the polynucleotide is linked to the expression control sequence in such a manner to enable expression of the polynucleotide. As used herein, the term "expression control sequence" means a DNA sequence that regulates the expression of the operably linked nucleic acid sequence in a certain host cell. Such the control sequence includes a promoter for performing transcription, an optional operator sequence for controlling transcription, a sequence encoding a suitable mRNA ribosome-binding site, and a sequence controlling termination. Vectors suitable to introduce the LOV1 gene into a plant cell include a Ti plasmid, a root-inducing (Ri) plasmid and a plant virus vector. Examples of the most suitable vector include but are not limited to binary vectors, such as pPZP, pGA and pCAMBIA series. Anyone skilled in the art can select a suitable vector for introducing the nucleic acid of the LOV1 gene of the present invention. Any vector capable of introducing the LOV1 gene sequence into plant cells can be used in the present invention.

The recombinant vector according to the present invention can be introduced into plant cells by known methods which include but are not limited to transformation using *Agrobacterium* species, particle gun bombardment, silicon carbide whiskers, sonication, electroporation and PEG (polyethyleneglycol) precipitation. Thus, the present invention provides a host cell transformed with the recombinant vector. Preferred examples of the host cell include bacteria, for example, *E. coli* or *Agrobacterium* sp.

Furthermore, the present invention provides a method for manipulating the flowering time of plants using the polynucleotide controlling the plant's flowering time. More particularly, the present invention provides the method for manipulating the flowering time of plants, wherein the polynucleotide of the present invention is overexpressed in the plants to delay the flowering time of the plants, or the expression of the polynucleotide in the plants is repressed to promote the flowering time of the plants.

For the overexpression of the polynucleotide of the present invention in plants, the polynucleotide is introduced into plants with or without the polynucleotide. As used herein, the term "overexpression" means the expression of the LOV1 gene at a level higher than that in wild-type plants. As a method for introducing the gene into a plant, there is a method of transforming a plant with an expression vector including the gene controlled by a promoter. Any promoter can be used if it can overexpress the gene inserted into the plant. Examples of the promoter may include but are not limited to 35S RNA and 19S RNA promoters of CaMV, a fill-length transcription promoter derived from Figwort mosaic virus (FMV), and a TMV coat protein promoter. Also, an ubiquitin promoter can be used to overexpress the LOV1 gene in a monocotyledon or a woody plant.

For the repression of expression of the polynucleotide of the present invention, a variety of methods known in the art can be used. The term "repression of expression" includes the repression of gene transcription and the repression of the translation into a protein. Also, it includes complete termination and reduction of the expression of the polynucleotide.

To repress the expression of a certain endogenous gene in plants, antisense molecules are most generally used. The mechanisms of the antisense molecules to repress the expression of a target gene include: repression of transcriptional initiation resulting from the formation of a triple strand; repression of transcription resulting from hybrid formed at the site where a local open loop structure was made by RNA polymerase; repression of transcription resulting from hybrid formation with the RNA being synthesized; repression of splicing resulting from hybrid formation at the junction between intron and exon; repression of splicing resulting from hybrid formation at the site of spliceosome formation; repression of mRNA translocation from the nucleus to the cytoplasm resulting from hybrid formation with mRNA; and the repression of translational initiation resulting from hybrid formation at the binding site for the translational initiation factors. Such antisense molecules repress the express of target gene by inhibiting the process of transcription, splicing or translation.

The antisense molecules, which are used in the present invention, may repress the expression of a target gene by any of the above mechanisms. Typical antisense molecules include triplex agent, ribozyme, RNAi, and antisense nucleic acid. The triplex agent is circularized around a double-strand DNA to form a triple helix, thereby repressing transcriptional initiation (Maher et al., *Antisense Res. and Dev.*, 1(3):227, 1991; and Helene, C. *Anticancer Drug Design*, 6(6):569, 1991). The ribozyme is a RNA molecule having the ability to specifically cleave other single-stranded RNA. The ribozyme can be manipulated such that it recognizes and sub-specifically cleave a certain nucleotide sequence within a RNA molecule (Cech, *J. Amer. Med Assn.*, 260:3030, 1998). Thus, a main advantage of this method using the ribozyme is that only mRNA with a certain sequence is inactivated since the ribozyme is sequence-specific. The method using RNAi is to repress the expression of a gene at a transcription level or post-transcription level using a hairpin-type oligomeric RNA, which acts in a base sequence-specific manner (Mette et al., *EMBO J.*, 19:5194–5201, 2000). The antisense nucleic acids are DNA or RNA molecules, which are complementary to at least a portion of a specific mRNA molecule (Weintraub, *Scientific American*, 262:40, 1990). In the cell, the antisense nucleic acids are hybridized to the corresponding mRNA, forming a double-stranded molecule. The antisense nucleic acids interfere with the translation of the mRNA (Marcus-Sakura, *Anal. Biochem.*, 172:289, 1988).

The method for manipulating the flowering time of plants of the present invention can be applicable as follows. The expression of the polynucleotide of the present invention can be repressed to promote the flowering time of horticultural plants such that flowers and seeds can be produced within a short time. Alternatively, the polynucleotide of the present invention can be overexpressed to delay the flowering time of agricultural plants so as to continuously induce the vegetative growth of the agricultural plants such that the production of useful portions from the agricultural plants can be increased.

The present invention is applicable to both monocotyledons and dicotyledons. Examples of the plants include: food crops, including rice, wheat, barley, corn, bean, potato, red bean, oat and American millet; vegetable crops, including *Arabidopsis*, Chinese cabbage, radish, red pepper, strawberry, tomato, watermelon, cucumber, cabbage, melon, pumpkin, Welsh onion, onion and carrot; industrial crops, including ginseng, tobacco, cotton, sesame, sugar cane, sugar beet, green perilla and rape; fruit trees, including apple tree, pear tree, jujube tree, peach, chinensis Planch, grape, mandrain orange, persimmons plum, apricot and banana; flowers, including rose, *Gladiolus, Gerbera*, carnation, mum, lily and tulip; and forage crops, including Ryegrass, red clover, Orchardgrass, Alfalfa, Tallfescue and Perenniaryegrass.

Also, the present invention provides a method for identifying a compound controlling the flowering time of plants using the polynucleotide of the present invention. More specifically, the present invention provides a method for identifying a compound controlling the flowering time of plants, the method comprising the steps of culturing a recombinant cell expressing the polynucleotide and a candidate substance, and measuring the effect of the candidate substance on the expression of the polynucleotide. The compound controlling the flowering time of plants may have the ability of promoting or inhibiting the expression of the polynucleotide. The effect of the candidate substance on the expression of the polynucleotide can be evaluated by a method known in the art, such as Northern blot or Western blot analysis. Examples of the compound controlling the flowering time of plants include peptides, polypeptides, peptidomimetics, compounds and biological agents.

Meanwhile, the polypeptide of the present invention can be converted into a probe or primer and advantageously used in the character improvement for flowering of plants and in the investigation of flowering-controlling genes in other plants by known genetic engineering techniques, such as DNA chip, protein chip, polymerase chain reaction, Northern blot analysis, Southern blot analysis, enzyme-Linked Immunosorbent assay and 2-D gel analysis.

Hereinafter, the present invention will be described in detail with reference to the following examples. However, the examples are given for illustrative purpose only and the scope of the present invention is not limited to or by the examples.

BEST MODE FOR CARRYING OUT THE INVENTION

EXAMPLE 1

Screening of Mutants with Delayed Flowering from *Arabidopsis thaliana*

In order to induce a mutation for *Arabidopsis thaliana*, pSKI015 (provided by Dr. Detlef Weigel, The Salk Institute, Calif., USA), activation tagging vector, was introduced into *Agrobacterium tumefaciens* strain GV3101 by electroporation using a micro pulser (Bio-Rad). Then, the *Agrobacterium* strain inserted with pSKI015 vector was selected in a medium containing kanamycine and carbenicillin. Wild type *Arabidopsis thaliana* (*Arabidopsis thaliana* ecotype Col-0) was transformed with the selected *Agrobacterium* strain according to a floral dip method (Clough et al., *Plant J.*, 16(6):735–743, 1998). The *Agrobacterium* strain carrying the pSKI015 vector was inoculated to a YEP medium containing gentamycin and ampicillin and cultured at 28° C. to an absorbance of 0.8. The cultured solution was centrifuged, and the precipitated cells were suspended in 5% sugar solution. Silwet L-77 was added to the solution to a concentration of 0.05% (500 µl/L), and a portion of *Arabidopsis thaliana* above soil was immersed in the solution for 5–7 seconds and then picked up. To maintain the plant at high humidity, the plant was covered and left to stand for 16–24 hours. The *Arabidopsis thaliana* transformed as described above continued to culture to harvest the next generation seeds. The seeds of wild type *Arabidopsis thaliana* and lov1-1D mutants were vernalized at 4° C. for 2–3 days, such that the germination time of the seeds became constant. The vernalized seeds were sowed on a port at given intervals and cultivated at 23° C. under long-day conditions (16-hr light/ 8-hr dark). When seed-leaves and two rosette leaves sprouted out, herbicide basta (ammonium glufosinate) was sprinkled two times a week for two weeks, and transgenic plants introduced with the pSKI015 were selected. The screened transgenic plants were cultivated in a greenhouse at 23° C., and mutants with delayed flowering were selected. Such mutants were termed lov1-1D mutants.

EXAMPLE 2

Examination of Changes in Flowering Time and Phenotype of Mutants with Delayed Flowering Changes in the flowering time and phenotype of the lov1-1D mutants selected in Example 1 were examined by comparison with those of wild type *Arabidopsis thaliana*. About 5 cm growth of a floral axis after its formation was used as the index of a flowering stage, and the number of primary rosette leaves and cauline leaves formed at this stage was used as the index of a flowering time.

As a results, in the lov1-1D mutant, the floral axis sprouted out after about 2 months, and in wild type *Arabidopsis thaliana*, the floral axis sprouted out after about 2–3 weeks. At a time when the floral axis sprouted from the mutants, it could be observed for wild type *Arabidopsis thaliana* that the leaves turned yellow and dried up, and the wild type was aged such that the seeds could be harvested. In some of the lov1-1D mutants, the floral axis did not sprout even after two months. Meanwhile, wild type *Arabidopsis thaliana* generally had 12–13 rosette leaves whereas the mutants had about 30–35 rosette leaves upon sprouting out of the floral axis (see FIG. 1A). This indicates that, in the lov1-1D mutants, their vegetative growth stage was lengthened while their flowering was delayed, as compared to those in the wild-type plant. Meanwhile, the lov1-1D mutants showed an abnormal silique shape as compared to the wild-type plant. The silique shape of the mutants was in the form of a short and blunt cudgel, due to an increase in carpel number (see FIG. 1B). This change in the silique shape of the mutants was similar to a phenotype observed in *Arabidopsis thaliana* where a FLC gene had been overexpressed (Hepworth S. R. et al., *EMBO J.* 21:4327–4337, 2002). From this similarity in phenotype, it was estimated that the gene overexpressed in the mutants of the present invention would have correlation with other genes controlling the flowering time of plants.

EXAMPLE 3

Cloning and Sequence Analysis of LOV1 Gene

To screen a gene around T-DNA activated by an enhancer in lov1-1D mutants, a gene around T-DNA was isolated by plasmid recovery. First, a total genome was isolated from the lov1-1D mutants using a DNeasy plant mini kit (QIAGENE®). Then, 2 µg of the genomic DNA was digested with a variety of the following restriction enzymes (New England Biolabs; NEB). Enzymes known as being used in recovering a base sequence in the around of the right border of T-DNA include KpnI, EcoRI and HindIII, and enzymes known as being used in recovering a base sequence in the around of the left border of T-DNA include BamHI, SpeI and NotI. Thus, treating the genomic DNA with each of the restriction enzymes showed that the genomic DNA was successfully recovered even upon plasmid recovery using HindIII. The digested DNA was treated with phenol-chloroform and self-ligated with T4-DNA ligase at 4° C. The ligated DNA was precipitated, dissolved in TE buffer solution, and then, *E. coli* DH5α cells (Bio-Rad) were transformed with the DNA solution by electroporation. The *E. coli* was added with 1 ml of LB medium (1% Trypton, 0.5% yeast extract, 0.5% NaCl, pH 7.0) and cultured at 37° C. for one hour. After the culturing, the cultured solution was plated on LB solid medium (prepared by adding 1.5% (w/v) bacto-agar to the LB medium) containing ampicillin, and cultured overnight at 37° C., after which colonies with antibiotic resistance were selected. The selected colonies were cultured in LB medium, and then, the DNA was isolated by alkaline lysis (Bimboim H. C. et al., *Nucleic Acids Res.*, 7:1513–1523, 1979). The plant DNA sequence located at the right border of a region inserted with T-DNA was determined with a DNA automatic sequencer (Perkin-Elmer, USA) and a Big dye terminator sequencing kit. The determined DNA sequence was analyzed with a sequence analysis program (Mac DNASIS program, Hitachi Software Engineering, America Ltd., San Bruno. Calif.), and an amino acid sequence was inferred from the base sequence. Also, the sequence homology between the analyzed gene sequence of the invention and the sequence of other known genes on a Genbank database was examined.

As a result, the isolated gene was about 8-kb apart from the right border of T-DNA containing a CaMV 35S enhancer. Moreover, a portion of the left boundary of T-DNA was reverse inserted into the right border end linked to the gene of *Arabidopsis thaliana* by several bases (see FIG. 2). The isolated gene had a total genome size of 2606 bp and an open reading frame (ORF) with an 1140 bp size encoding 379 amino acids. Furthermore, it could be found that the gene of the present invention had homology with the NAM, CUC1 and CUC2 genes of *Perunia hybrida*, which are members of the NAC domain gene family (FIG. 3). Namely, the NAC domain was conserved in the first and second exons between the NAC domain gene families (Duval et al., *Plant Molecular Biology*, 50:237–248, 2002). Therefore, the present inventors termed the inventive gene "LOV1" (Long Vegetative phase 1). The total genome sequence and cDNA of the LOV1 gene according to the present invention are shown in SEQ ID NO: 3 and SEQ ID NO: 1, respectively, and the amino acid sequence of the LOV1 protein is shown in SEQ ID NO: 2.

EXAMPLE 4

Examination of Expression of LOV1 Gene in Wild Type *Arabidopsis thaliana* and lov1-1D Mutants In order to confirm if the LOV1 gene isolated in Example 3 is actually overexpressed in the lov1-1D mutants by the CaMV 35S enhancer as compared to that in wild type *Arabidopsis thaliana*, Northern blot analysis was performed with a probe specific to the LOV1 gene. First, from wild type *Arabidopsis thaliana* and lov1-1D mutants, which had been cultured for 18 days under the same condition, the respective RNAs were isolated by a RNTeasy plant kit (QIAGEN®). Each 10 µg of the RNAs was loaded on 1% formaldehyde agarose gel absorbed with 1× MOPS buffer (200 mM MOPS, pH 7.0, 50 mM NaOAc, 10 mM EDTA), and it was treated with EtBr (ethidium bromide) and then transferred to a nylon membrane (Hybond N+ membrane) by 20×SSC. The nylon membrane was lightly washed with 2×SSC and dried. The RNA transferred to the nylon membrane was treated with 1 mM EDTA, 0.5M sodium phosphate, 1× Denhardt's solution, 1% BSA and 7% SDS. The treated RNA was hybridized overnight with a labeled probe specific to the LOV1 gene at 65° C. At the end of the hybridization, the nylon membrane was washed with 2×SSC and 0.1% SDS at 65° C. for 5 minutes, and then with 0.2×SSC and 0.1% SDS at the same temperature for 5 minutes. The washed nylon membrane was dried and exposed to an X-ray film to detect bands sensitized with radiations. The probe used in the above hybridization was prepared by random primer labelling using a Prime-a-gene system (Promega) and [α-$^{32}$P] dATP.

As a result, it was revealed that the LOV1 gene was expressed at a higher level in the lov1-1D mutants than that in wild type *Arabidopsis thaliana* (see FIG. 4).

EXAMPLE 5

Expression Pattern of LOV1 Gene in *Arabidopsis thaliana*

RNA was extracted from various tissues of wild type *Arabidopsis thaliana* of a reproductive state, and subjected to Northern blot analysis with a probe specific to the LOV1 gene, to examine the spatial distribution pattern of LOV1 gene transcripts. RNA was isolated from the tissues of floral buds, flowers, siliques, cauline leaves, rosette leaves and roots of wild type *Arabidopsis thaliana* in the same manner as in Example 4. Northern blot analysis was performed using the isolated RNA in the same manner as in Example 4.

Also, *Arabidopsis thaliana* was transformed with a LOV1 promoter-GUS (beta-glucuronidase) gene fusion construct, and GUS gene activity was analyzed to confirm the expression pattern of the LOV1 gene. The LOV1 promoter-GUS gene fusion construct was prepared as follows. PCR amplification of the genomic DNA of *Arabidopsis thaliana* as a template was performed using a forward primer (SEQ ID NO: 4) and a reverse primer (SEQ ID NO: 5) to amplify the promoter region of the LOV1 gene. In the PCR amplification, GeneAMP PCR system 9700 was used and 35 cycles each consisting of one minute at 94° C., one minute at 60° C., and 2 minutes at 72° C. were performed.

```
                                         (SEQ ID NO:4)
LOV1 forward primer:
5'-AATAGATCTGGTACGCGACATCCATATTGAAA-3'

(SEQ ID NO:5)
LOV1 reverse primer:
5'-AATAGATCTCATGGGAATGATGCTTGTTGTG-3'
```

Figure 5:
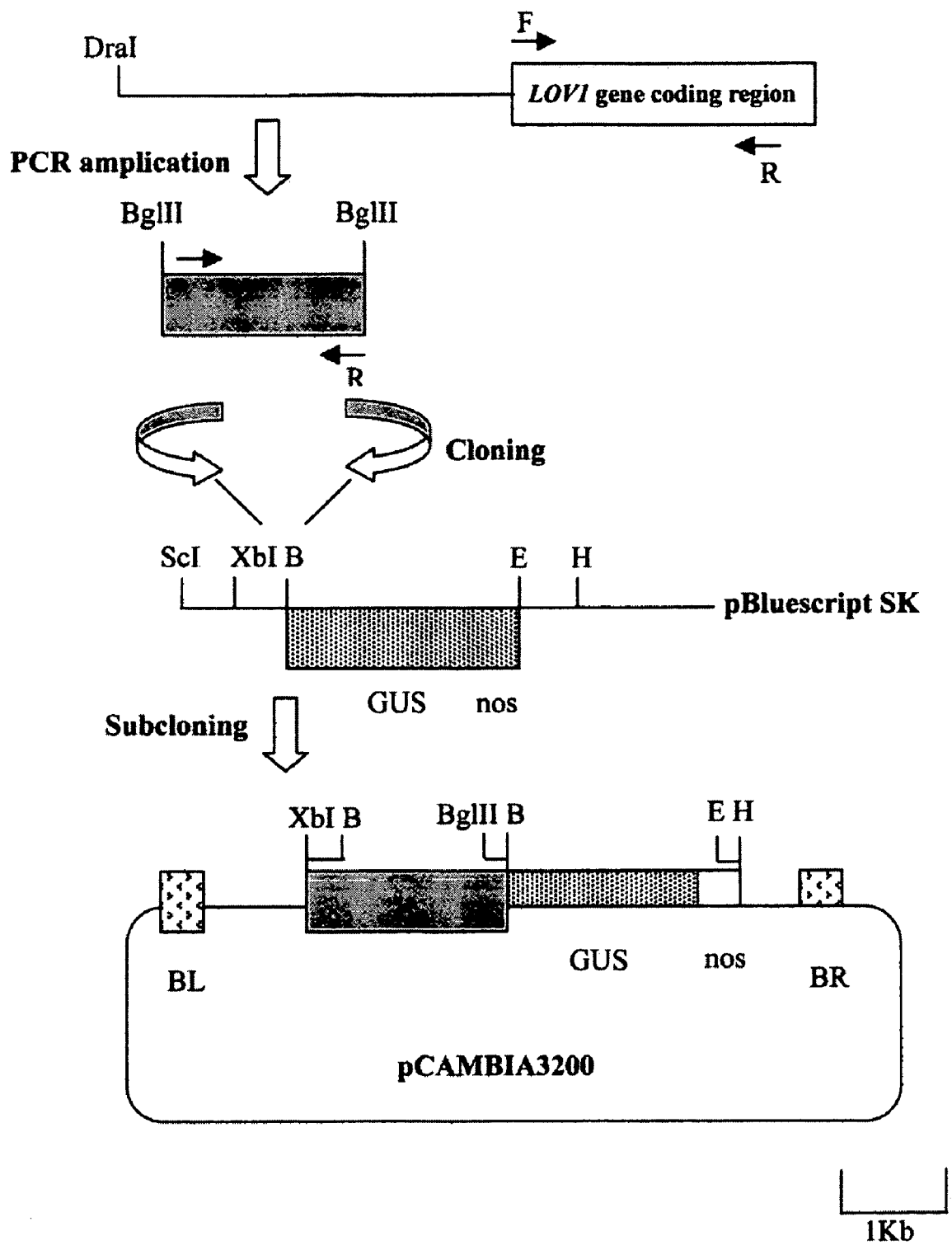
FIG. 5 is a schematic diagram showing a process for constructing a recombinant plasmid pCAMBIA3200 comprising a LOV1 promoter-GUS gene fusion construct (F: forward, R: reverse, BL: left border, BR: right border).

The amplified LOV1 gene promoter was cloned into a pGEM®-T Easy vector (Promega). It was digested with BgIII, and its fragment was linked to a pBluescript vector containing a GUS-nos gene. The LOV1 promoter::GUS-nos fragment in the pBluescript vector was subcloned into pCAMBIA3200, binary vector (see FIG. 5). Using the *Agrobacteriun* transformed with the binary vector in the same manner as in Example 1, the LOV1 promoter::GUS recombinant plasmid was introduced into wild type *Arabidopsis thaliana*. GUS activity in each tissue of the transgenic plant was measured by GUS histochemical analysis using 5-bromo-4-chloro-3-indoly glucuronide (X-Gluc). Also, while the transgenic plant was cultivated for 40 days, the expression pattern of the LOV1 gene according to time was examined. The GUS histochemical analysis performed as described above included a partial modification to a known GUS histochemical analysis method (Jefferson R. A. et al., *EMBO J.*, 6:3901–3907, 1987). Each tissue sample obtained from the transgenic plant was immersed in GUS reaction solution (1 mM X-Gluc, 50 mM sodium phosphate, pH 7.0, 0.1% typton X-100) for 12 hours and then washed with ethanol. The sample showing deep blue color was cut with Microtome (Lecia) and observed with Nikon SMZ 10A stereomicroscope (Nikon Co., Tokyo).

Furthermore, the shoot apical tissues of stems and leaves obtained from the transgenic plant were finely cut, and their cross sections were observed with a microscope. The shoot apical tissues of the leaves and stems from the plant were immediately dipped in FAA fixative solution (50% ethanol, 5% acetic acid and 3.7% formaldehyde) and then left to stand under vacuum for 15 minutes. The fixed tissues were left to stand at room temperature for 16 hours in a state where they were dipped in the FAA fixative solution. Then, the fixed tissues were treated with ethanol to remove water and filled with xylene. The tissues from which water had been removed were filled with paraplast for at least three days and cut into 8 μm cross-sections using Microtome (Leica). The cross-sections were attached to a slide glass (Sigma) and placed in a slide warmer (Fisher) at 45° C. overnight The slide glass to which the tissues had been firmly attached was immersed in xylene for 30 minutes to remove paraffin and then observed with a stereomicroscope.

Figure 6:
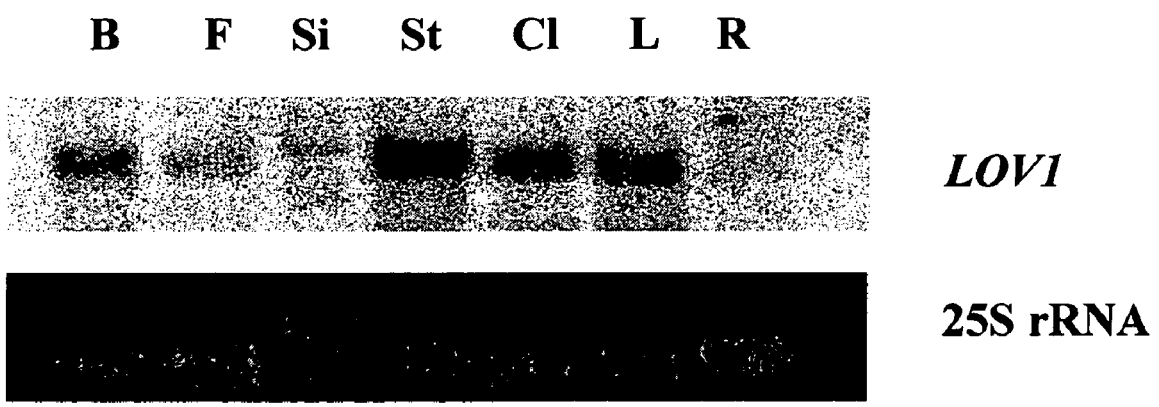
FIG. 6 is the result of Northern blot analysis showing the expression pattern of a LOV1 gene in each tissue of wild type *Arabidopsis thaliana* (25S rRNA: internal control, B: floral bud, F: flowers, Si: siliques, St: stems, Cl: cauline leaves, L: rosette leaves, R: roots).

Northern blot analysis was performed using the RNA extracted from each tissue of wild type *Arabidopsis thaliana* and the analysis results showed that the LOV1 gene was generally in all the tissues, and particularly, expressed mainly in the stems (see FIG. 6).

Figure 7A:
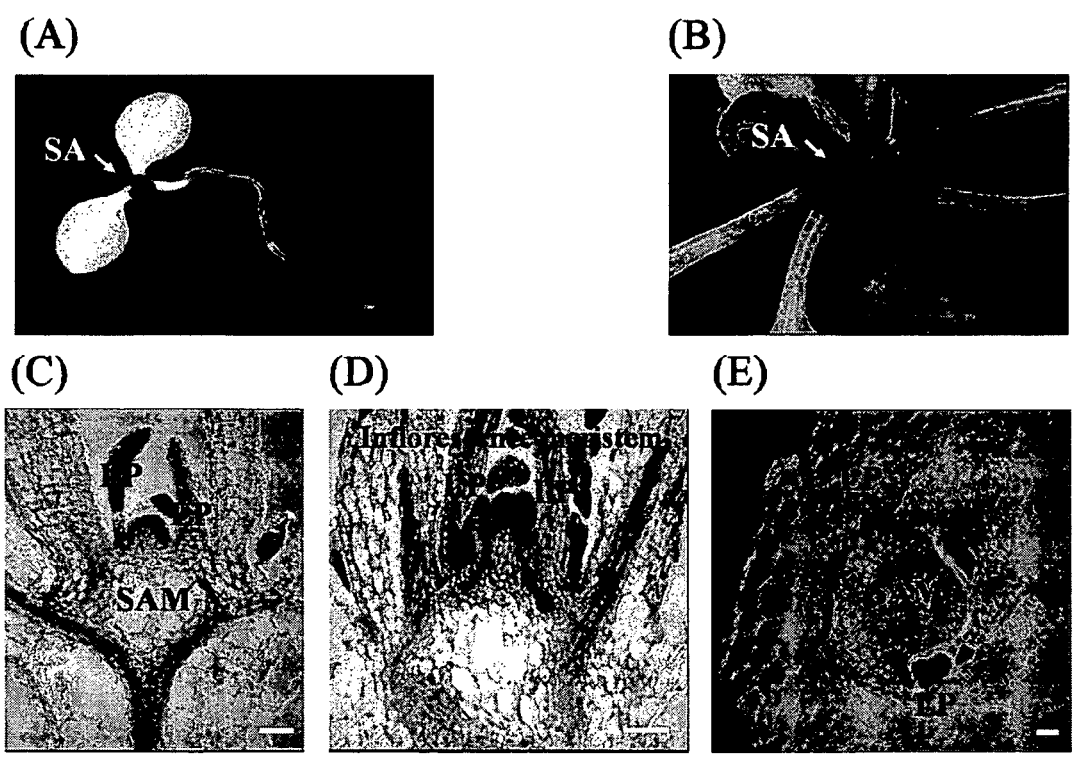
FIG. 7A shows the results of GUS activity analysis in the shoot apex meristem and leaf primorida of a transgenic plant introduced with a LOV1 promoter-GUS gene fusion construct (A: seedling, B: the shoot apex meristem and leaf primorida of vegetative growth stage plants, C: the longitudinal sections of the shoot apical meristems of 15-day old plants, D: the longitudinal sections of floral meristem, E: the transversal sections of floral meristem, SA: shoot apex, LP: leaf primorida; SAM: shoot apical meristem, scale bar: 10 μm).
Figure 7C:
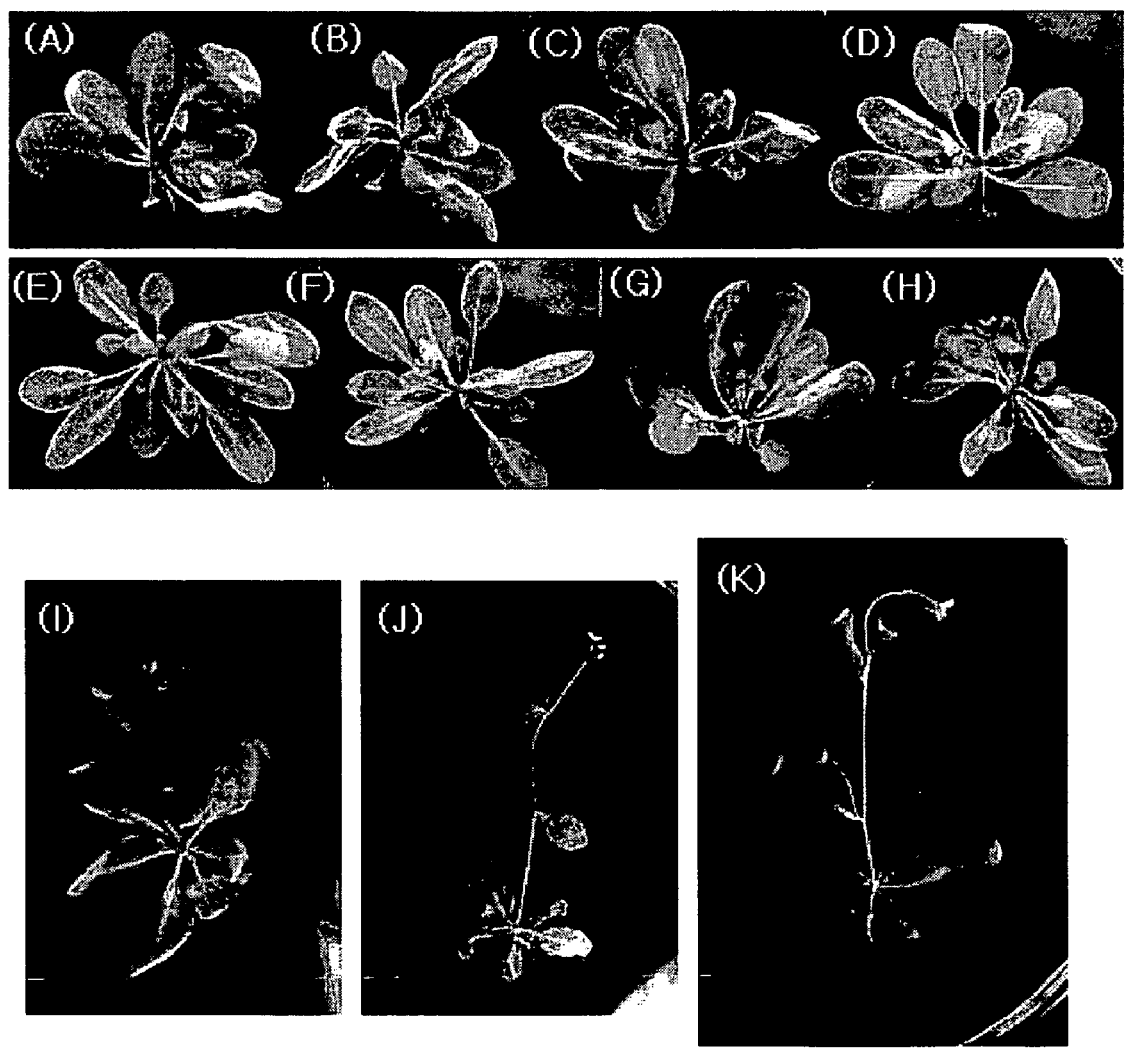
FIG. 7C shows the results of analysis of GUS activity according to time of a transgenic plant introduced with a LOV1 promoter-GUS gene fusion construct (A: 20 days, B: 21 days, C: 23 days, D: 25 days, E: 27 days, F: 29 days, G: 31 days, H: 33 days, I: 35 days, J: 37 days, K: 40 days).

GUS activity in *Arabidopsis thaliana* transformed with the LOV1 promoter and GUS fusion construct appeared mainly in the shoot apical tissue. It was observed that the LOV1 gene was strongly expressed in the shoot apical meristem, and also expressed in the young leaf primorida. However, the GUS activity did not appear in the completely unfolded leaves. When the shoot apical tissues of stems and leaves obtained from the transgenic plant were finely cut in a longitudinal direction, the GUS activity appeared in the shoot apical meristems. When they were cut in a transverse direction, the GUS activity appeared in the leaf primorida and the shoot apical meristem (see FIG. 7A). The GUS activity also appeared in the inflorescence meristem and the axillary meristem (see FIG. 7B). Such results suggest that the LOV1 gene is expressed in rapidly growing tissues and immature tissues at a high expression level. It was also observed that the expression of the LOV1 gene occurred during embryogenesis (see FIG. 7B) and continued even after the occurrence of flowering, i.e., even 20–21 days after the occurrence of flowering (see FIG. 7C).

This expression pattern of the LOV1 gene is similar to the expression pattern of an AGL20 gene. This suggests that the LOV1 gene will have genetic correlation with other genes controlling the flowering time of plants.

EXAMPLE 6

Comparison of Anatomical Cross-sections of Shoot Apical Meristems and Leaves Between Wild Type *Arabidopsis Thaliana* and lov1-1D Mutants In order to examine the difference in anatomical structure between wild type *Arabidopsis thaliana* and lov1-1D mutants, 9-day old shoot apical meristems and leaves were cut in the same manner as in Example 5, and their cross-sections were observed with Nikon SMZ 10A stereomicroscope (Nikon Co., Tokyo).

Figure 9:
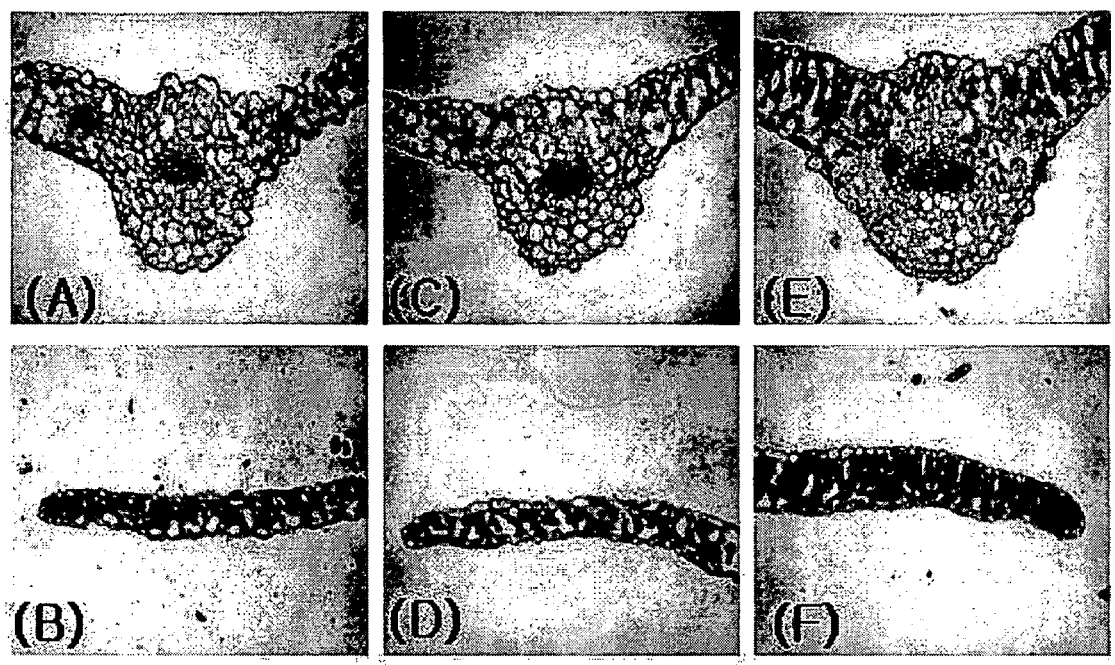
FIG. 9 is a stereomicroscopic photograph for the cross-sections of leaves of wild type *Arabidopsis thaliana* and lov1-1D mutants (A and B: wild-type plant, C and D: lov1-1D mutants at the same development stage as the wild-type plant, E and F: leaves produced at a late time in lov1-1D mutants, A, C and E: the longitudinal sections of vasculatures, B, D and F: the longitudinal sections of leaf ends, scale bar: 20 μm).

As a result, it was showed that the longitudinal-sections of shoot apical meristems of the lov1-1D mutants were somewhat larger and greater than those of the wild type plant. It was thought that this was because the cell size of shoot apical meristems of the lov1-1D mutants was increased as compared to the wild-type plant (see FIG. 8). Also, although there was clear difference in cross-sections of the leaf between the wild-type plant and the mutant plant that are at the same development stage, it was observed that the cross-sections of the leaves of the mutant plant, which was produced at a late time had increased cell size and number as compared to the wild-type plant (FIG. 9). It was thought that this result was because the LOV1 gene was overexpressed in the mutant plants. From this expression pattern of the LOV1 gene, it could be assumed that, while the plants were converted to the flowering stage, the LOV1 gene performed an important function in the shoot apical meristems and leaves of the plants. Particularly, from the result showing that the number of the mutant plant leaves was increased due to the overexpression of the LOV1 gene, it could be confirmed again that, in the mutants, their vegetative growth period was lengthened while their flowering was delayed, as compared to the wild-type plant.

EXAMPLE 7

Examination of Interactions Between LOV1 Gene and AGL20 Gene, and Between LOV1 Gene and FLC Gene Examination was performed on whether the LOV1 gene isolated in the present invention interacts with other genes AGL20 and FLC controlling the flowering time of plants. The AGL20 gene is known to promote flowering and to be repressed by the FLC gene. The FLC gene is a strong repressor of flowering that binds to the promoter of the AGL20 gene, the MADS-box flowering-time promoter gene, and represses the AGL20 gene (Hepworth S. R. et al., *EMBO J.* 21:4327–4337, 2002; and Michael S. D. et al., *Plant Cell,* 11:949–956, 1999). By the present inventors, the expression levels of the AGL20 and FLC genes in the lov1-1D mutants were examined by Northern blot analysis using probes specific to the respective genes. The specific probes were prepared from the known sequence of the FLC gene (Michaels and Amasino, *Plant Cell,* 11: 949–956, 1999), and the known sequence of the AGL20 gene (Lee et al., *Genes and Development* 14: 2366–2376, 2000), respectively, in the following manner.

```
                                        (SEQ ID NO:6)
    FLC forward primer:
    5'-CCCGTTAACTGAACCCAAACCTGAGGA-3'

(SEQ ID NO:7)
    FLC reverse primer:
    5'-CCACTAGTCGCCCTTATCAGCGGA-3'

(SEQ ID NO:8)
    AGL20 forward primer:
    5'-CCCGTTAACATGGTGAGGGGCAAAACT-3'

(SEQ ID NO:9)
    AGL20 reverse primer:
    5'-CCCGTTAACTCACTTTCTTGAAGAACAAGG-3'
```

The Northern blot analysis was performed in the same manner as in Example 4. Meanwhile, when flowering in wild type *Arabidopsis thaliana* is initiated, the lov1-1D mutant is still in the vegetative growth stage. Thus, for use in the experiment, RNAs were isolated from the wild type and mutant plants, on 18 days after cultivation when a floral axis in the wild-type plant did not sprout.

As a result, it was showed that the expression of the AGL20 gene in the lov1-1D mutant was reduced as that in the wild-type plant, but the expression levels of the FLC gene were similar between the wild-type plant and the mutant plant. This result suggests that the overexpresssion of the LOV1 gene reduces the expression of the AGL20 gene to delay the flowering of plants (see FIG. 10).

Figure 11:
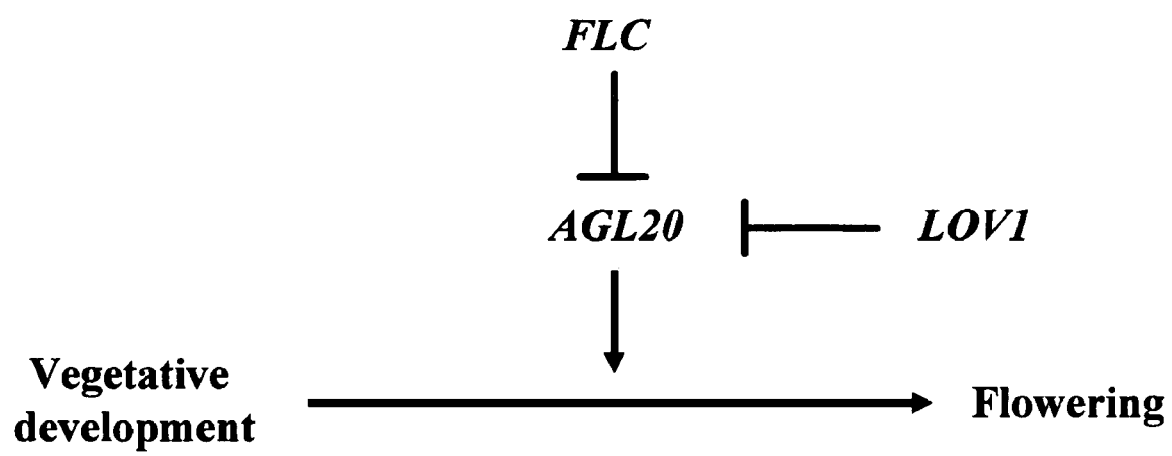
FIG. 11 is a schematic diagram showing the correlations between a LOV1 gene isolated of the present invention and AGL20 gene, and between the LOV1 and FLC gene. An arrow indicates promotion, and a T-shaped bar indicates repression.

In conclusion, it could be found that the LOV1 gene performed an important function in the shoot apical meristems during the conversion of plants from vegetative growth to reproductive growth, and downregulated the flowering-promoting gene AGL20 on a complex genetic network that determines flowering (see FIG. 11).

The entire disclosure of Korean Patent Application No. 10-2003-0010772, filed on Feb. 20, 2003 including its specification, claims, drawings and summary are incorporated herein by reference in its entirety.

What is claimed is:

1. A method for delaying the flowering time of plants, comprising the step of introducing into plants an isolated polynucleotide encoding a polypeptide having the amino acid sequence of SEQ ID NO:2, wherein the polynucleotide is operably linked to an expression control sequence, wherein the polynucleotide is expressed in the plants and flowering time is delayed, when compared to wild-type plants.

2. The method of claim 1, wherein the plants are monocotyledon or dicotyledon.

3. A method for preparing plants having delayed flowering time, comprising the step of introducing into plants an isolated polynuleotide encoding a polypeptide having the amino acid sequence of SEQ ID NO:2, wherein the polynucleotide is operably linked to an expression control sequence and overexpressing the polynucleotide, wherein flowering time is delayed compared to wild-type plants.

4. A plant having delayed flowering time, wherein the plant is prepared by the method of claim 3.

5. A plant tissue or seed derived from the plant of claim 4, wherein the seed comprises the introduced polynucleotide encoding a polypeptide having the amino acid sequence of SEQ ID NO: 2.

* * * * *

SEQUENCE LISTING

<160> NUMBER OF SEQ ID NOS: 9

<210> SEQ ID NO 1
<211> LENGTH: 1140
<212> TYPE: DNA
<213> ORGANISM: Arabidopsis thaliana
<220> FEATURE:
<221> NAME/KEY: CDS
<222> LOCATION: (1)...(1137)
<223> OTHER INFORMATION: cDNA of LOV1 gene

<400> SEQUENCE: 1

```
atg gca att gta tcc tcc aca aca agc atc att ccc atg agt aac caa      48
Met Ala Ile Val Ser Ser Thr Thr Ser Ile Ile Pro Met Ser Asn Gln
 1               5                  10                  15 gtc aac aat aac gaa aaa ggt ata gaa gac aat gat cat aga ggc ggc      96
Val Asn Asn Asn Glu Lys Gly Ile Glu Asp Asn Asp His Arg Gly Gly
             20                  25                  30 caa gag agt cat gtc caa aat gaa gat gaa gct gat gat cat gat cat     144
Gln Glu Ser His Val Gln Asn Glu Asp Glu Ala Asp Asp His Asp His
         35                  40                  45 gac atg gtc atg ccc gga ttt aga ttc cat cct acc gaa gaa gaa ctc     192
Asp Met Val Met Pro Gly Phe Arg Phe His Pro Thr Glu Glu Glu Leu
     50                  55                  60 ata gag ttt tac ctt cgc cga aaa gtt gaa ggc aaa cgc ttt aat gta     240
Ile Glu Phe Tyr Leu Arg Arg Lys Val Glu Gly Lys Arg Phe Asn Val
 65                  70                  75                  80 gaa ctc atc act ttc ctc gat ctt tat cgc tat gat cct tgg gaa ctt     288
Glu Leu Ile Thr Phe Leu Asp Leu Tyr Arg Tyr Asp Pro Trp Glu Leu
                 85                  90                  95 cct gct atg gcg gcg ata gga gag aaa gag tgg tac ttc tat gtg cca     336
Pro Ala Met Ala Ala Ile Gly Glu Lys Glu Trp Tyr Phe Tyr Val Pro
            100                 105                 110 aga gat cgg aaa tat aga aat gga gat aga ccg aac cga gta acg act     384
Arg Asp Arg Lys Tyr Arg Asn Gly Asp Arg Pro Asn Arg Val Thr Thr
        115                 120                 125 tca gga tat tgg aaa gcc acc gga gct gat agg atg atc aga tcg gag     432
Ser Gly Tyr Trp Lys Ala Thr Gly Ala Asp Arg Met Ile Arg Ser Glu
    130                 135                 140 act tct cgg cct atc gga tta aag aaa acc cta gtt ttc tac tct ggt     480
Thr Ser Arg Pro Ile Gly Leu Lys Lys Thr Leu Val Phe Tyr Ser Gly
145                 150                 155                 160 aaa gcc cct aaa ggc act cgt act agt tgg atc atg aac gag tat cgt     528
Lys Ala Pro Lys Gly Thr Arg Thr Ser Trp Ile Met Asn Glu Tyr Arg
                165                 170                 175 ctt ccg cac cat gaa acc gag aag tac caa aag gct gaa ata tca ttg     576
Leu Pro His His Glu Thr Glu Lys Tyr Gln Lys Ala Glu Ile Ser Leu
            180                 185                 190 tgc cga gtg tac aaa agg cca gga gta gaa gat cat cca tcg gta cca     624
Cys Arg Val Tyr Lys Arg Pro Gly Val Glu Asp His Pro Ser Val Pro
        195                 200                 205 cgt tct ctc tcc aca aga cat cat aac cat aac tca tcg aca tca tcc     672
Arg Ser Leu Ser Thr Arg His His Asn His Asn Ser Ser Thr Ser Ser
```

```
cgt tta gcc tta aga caa caa caa cac cat tca tcc tcc tct aat cat    720
Arg Leu Ala Leu Arg Gln Gln Gln His His Ser Ser Ser Ser Asn His
225                 230                 235                 240 tcc gac aac aac ctt aac aac aac aac atc aac aat ctc gag aag        768
Ser Asp Asn Asn Leu Asn Asn Asn Asn Ile Asn Asn Leu Glu Lys
                245                 250                 255 ctc tcc acc gaa tat tcc ggc gac ggc agc aca aca acg acc aca        816
Leu Ser Thr Glu Tyr Ser Gly Asp Gly Ser Thr Thr Thr Thr Thr
                260                 265                 270 aac agt aac tct gac gtt acc att gct cta gcc aat caa aac ata tat    864
Asn Ser Asn Ser Asp Val Thr Ile Ala Leu Ala Asn Gln Asn Ile Tyr
275                 280                 285 cgt cca atg cct tac gac aca agc aac aac aca ttg ata gtc tct acg    912
Arg Pro Met Pro Tyr Asp Thr Ser Asn Asn Thr Leu Ile Val Ser Thr
290                 295                 300 aga aat cat caa gac gat gat gaa act gcc att gtt gac gat ctt caa    960
Arg Asn His Gln Asp Asp Asp Glu Thr Ala Ile Val Asp Asp Leu Gln
305                 310                 315                 320 aga cta gtt aac tac caa ata tca gat gga gcg aca acg cta atg cct   1008
Arg Leu Val Asn Tyr Gln Ile Ser Asp Gly Ala Thr Thr Leu Met Pro
                325                 330                 335 caa act caa gcg gcg tta gct atg aac atg att cct gca gga acg att   1056
Gln Thr Gln Ala Ala Leu Ala Met Asn Met Ile Pro Ala Gly Thr Ile
                340                 345                 350 cca aac aat gct ttg tgg gat atg tgg aat cca ata gta cca gat gga   1104
Pro Asn Asn Ala Leu Trp Asp Met Trp Asn Pro Ile Val Pro Asp Gly
                355                 360                 365 aac aga gat cac tat act aat att cct ttt aag taa                   1140
Asn Arg Asp His Tyr Thr Asn Ile Pro Phe Lys
370                 375

<210> SEQ ID NO 2
<211> LENGTH: 379
<212> TYPE: PRT
<213> ORGANISM: Arabidopsis thaliana

<400> SEQUENCE: 2

Met Ala Ile Val Ser Ser Thr Thr Ser Ile Ile Pro Met Ser Asn Gln
1               5                   10                  15

Val Asn Asn Asn Glu Lys Gly Ile Glu Asp Asn Asp His Arg Gly Gly
                20                  25                  30

Gln Glu Ser His Val Gln Asn Glu Asp Glu Ala Asp Asp His Asp His
        35                  40                  45

Asp Met Val Met Pro Gly Phe Arg Phe His Pro Thr Glu Glu Glu Leu
    50                  55                  60

Ile Glu Phe Tyr Leu Arg Arg Lys Val Glu Gly Lys Arg Phe Asn Val
65              70                  75                  80

Glu Leu Ile Thr Phe Leu Asp Leu Tyr Arg Tyr Asp Pro Trp Glu Leu
                85                  90                  95

Pro Ala Met Ala Ala Ile Gly Glu Lys Glu Trp Tyr Phe Tyr Val Pro
                100                 105                 110

Arg Asp Arg Lys Tyr Arg Asn Gly Asp Arg Pro Asn Arg Val Thr Thr
        115                 120                 125

Ser Gly Tyr Trp Lys Ala Thr Gly Ala Asp Arg Met Ile Arg Ser Glu
    130                 135                 140

Thr Ser Arg Pro Ile Gly Leu Lys Lys Thr Leu Val Phe Tyr Ser Gly
145                 150                 155                 160
```

Lys Ala Pro Lys Gly Thr Arg Thr Ser Trp Ile Met Asn Glu Tyr Arg
            165                 170                 175

Leu Pro His His Glu Thr Glu Lys Tyr Gln Lys Ala Glu Ile Ser Leu
            180                 185                 190

Cys Arg Val Tyr Lys Arg Pro Val Glu Asp His Pro Ser Val Pro
            195                 200                 205

Arg Ser Leu Ser Thr Arg His His Asn His Asn Ser Ser Thr Ser Ser
            210                 215                 220

Arg Leu Ala Leu Arg Gln Gln Gln His His Ser Ser Ser Ser Asn His
225                 230                 235                 240

Ser Asp Asn Asn Leu Asn Asn Asn Asn Ile Asn Asn Leu Glu Lys
            245                 250                 255

Leu Ser Thr Glu Tyr Ser Gly Asp Gly Ser Thr Thr Thr Thr Thr
            260                 265                 270

Asn Ser Asn Ser Asp Val Thr Ile Ala Leu Ala Asn Gln Asn Ile Tyr
            275                 280                 285

Arg Pro Met Pro Tyr Asp Thr Ser Asn Asn Thr Leu Ile Val Ser Thr
            290                 295                 300

Arg Asn His Gln Asp Asp Glu Thr Ala Ile Val Asp Asp Leu Gln
305                 310                 315                 320

Arg Leu Val Asn Tyr Gln Ile Ser Asp Gly Ala Thr Thr Leu Met Pro
            325                 330                 335

Gln Thr Gln Ala Ala Leu Ala Met Asn Met Ile Pro Ala Gly Thr Ile
            340                 345                 350

Pro Asn Asn Ala Leu Trp Asp Met Trp Asn Pro Ile Val Pro Asp Gly
            355                 360                 365

Asn Arg Asp His Tyr Thr Asn Ile Pro Phe Lys
            370                 375

```
<210> SEQ ID NO 3
<211> LENGTH: 2606
<212> TYPE: DNA
<213> ORGANISM: Arabidopsis thaliana
<220> FEATURE:
<221> NAME/KEY: gene
<222> LOCATION: (1)...(2606)
<223> OTHER INFORMATION: genomic DNA of LOV1 gene

<400> SEQUENCE: 3
atggcaattg tatcctccac aacaagcatc attcccatga gtaaccaagt caacaataac     60
gaaaaaggta tagaagacaa tgatcataga ggcggccaag agagtcatgt ccaaaatgaa    120
gatgaagctg atgatcatga tcatgacatg gtcatgcccg gatttagatt ccatcctacc    180
gaagaagaac tcatagagtt ttaccttcgc cgaaaagttg aaggcaaacg ctttaatgta    240
gaactcatca ctttcctcga tctttatcgc tatgatcctt gggaacttcc tggtaaatat    300
acattcacat aaacacacat aaatcatctc aaactatttg gaaatcttaa tttctattca    360
tatgttaaga tctttcttct ctcttatcac tttctctctc tatttctttt tttttaacct    420
atatatgtac ctacctcctt atgaagtatt actatgtcga tcgttaacaa ttctcaatat    480
ctttaaacgc ttctccctct ttagtttctt tcttaaatta acctaattaa acaacctaca    540
tatatatcat aagatataca aatatgtgta tgttttcata attagcttat gtatgtttaa    600
tcatagatat atgtatatgc agctatggcg gcgataggag agaaagagtg gtacttctat    660
gtgccaagag atcggaaata tagaaatgga gatagaccga accgagtaac gacttcagga    720
```

-continued

```
tattggaaag ccaccggagc tgataggatg atcagatcgg agacttctcg gcctatcgga      780
ttaaagaaaa ccctagtttt ctactctggt aaagcccta aaggcactcg tactagttgg       840
atcatgaacg agtatcgtct tccgcaccat gaaaccgaga agtaccaaaa ggtataaatt      900
ctactataac tctatatata tcctattcat acatacatag atataaccct agctaggtgg     960
tgaggccttt aaaattgaaa ttaatcccta gacagtttga attttttctt ttttgactag     1020
ttttatttat ttattttgga attgattcga taagatcaaa atacttgtg aatggactaa      1080 atgtcaggcg gcgtttgcgc ttaaatccag aaaaatgttc atgtcatatg cgtgaactct     1140
ttaaattgct agacatggcc catatgttat agtagaatac attaatagat agatgcatac     1200
acatatatat aaacacacaa gtatcacact cgacattcat atccttaat tctgcagaga      1260 catagttagt ttttcttaca atttatgaca tgaatgttcc tgctcttcct cacattaatt    1320
catgtcttct atttaagtta cccaacattt tttgaaataa tttggcatat atgaattata    1380
ccaacatatt tatatgcgaa catttaaaat ctatacgaat gataacggtt tatggagtag    1440
accgaaaaaa tattatgtat acggaaaatg acaatggata gataaataca ttttttgggc   1500
tctttcgact tatatgtcgt caccatttga aaccataaat ttataaaatt ttctatgtat   1560
atatatgata ttatgatgta tgcataagac agctaaaaca acagggttga cataattatc   1620
tatgtgtatg tattgcacat tcacttgtac taataaaact aaaattacgc aattaaatat    1680
ataaaaaata ataaatataa tcatcttaat tatatttgca ttgttacgtc atatgatagt    1740
actctaaatt tcttctaaac gtgctatctt tttttgctaa tgctaacttt acatagtttg    1800
tgaatcttct ttcaaaacca tatcttcgat aaatgatatt tttcatagat attgttagtc    1860
tatatttgat aatttgatat atgtatcaag tctctaatca atgtgctcat gtataattat    1920
aggctgaaat atcattgtgc cgagtgtaca aaaggccagg agtagaagat catccatcgg   1980
taccacgttc tctctccaca agacatcata accataactc atcgacatca tcccgtttag   2040
ccttaagaca acaacaacac cattcatcct cctctaatca ttccgacaac aaccttaaca   2100
acaacaacaa catcaacaat ctcgagaagc tctccaccga atattccggc gacggcagca   2160
caacaacaac gaccacaaac agtaactctg acgttaccat tgctctagcc aatcaaaaca   2220
tatatcgtcc aatgccttac gacacaagca acaacacatt gatagtctct acgagaaatc    2280
atcaagacga tgatgaaact gccattgttg acgatcttca aagactagtt aactaccaaa   2340
tatcagatgg aggtaacatc aatcaccaat actttcaaat tgctcaacag tttcatcata    2400
ctcaacaaca aaatgctaac gcaaacgcat tacaattggt ggctgcggcg actacagcga   2460
caacgctaat gcctcaaact caagcggcgt tagctatgaa catgattcct gcaggaacga   2520
ttccaaacaa tgctttgtgg gatatgtgga atccaatagt accagatgga aacagagatc   2580
actatactaa tattcctttt aagtaa                                         2606
```

<210> SEQ ID NO 4
<211> LENGTH: 32
<212> TYPE: DNA
<213> ORGANISM: Artificial Sequence
<220> FEATURE:
<223> OTHER INFORMATION: Sense primer of LOV1

<400> SEQUENCE: 4
aatagatctg gtacgcgaca tccatattga aa                                   32

<210> SEQ ID NO 5
<211> LENGTH: 31

```
<212> TYPE: DNA
<213> ORGANISM: Artificial Sequence
<220> FEATURE:
<223> OTHER INFORMATION: Antisense primer of LOV1

<400> SEQUENCE: 5
aatagatctc atgggaatga tgcttgttgt g                          31

<210> SEQ ID NO 6
<211> LENGTH: 27
<212> TYPE: DNA
<213> ORGANISM: Artificial Sequence
<220> FEATURE:
<223> OTHER INFORMATION: Sense primer of FLC

<400> SEQUENCE: 6
cccgttaact gaacccaaac ctgagga                               27

<210> SEQ ID NO 7
<211> LENGTH: 24
<212> TYPE: DNA
<213> ORGANISM: Artificial Sequence
<220> FEATURE:
<223> OTHER INFORMATION: Antisense primer of FLC

<400> SEQUENCE: 7
ccactagtcg cccttatcag cgga                                  24

<210> SEQ ID NO 8
<211> LENGTH: 27
<212> TYPE: DNA
<213> ORGANISM: Artificial Sequence
<220> FEATURE:
<223> OTHER INFORMATION: Sense primer of AGL20

<400> SEQUENCE: 8
cccgttaaca tggtgagggg caaaact                               27

<210> SEQ ID NO 9
<211> LENGTH: 30
<212> TYPE: DNA
<213> ORGANISM: Artificial Sequence
<220> FEATURE:
<223> OTHER INFORMATION: Antisense primer of AGL20

<400> SEQUENCE: 9
cccgttaact cactttcttg aagaacaagg                            30
```